United States Patent [19]
Tu et al.

[11] Patent Number: 6,123,718
[45] Date of Patent: Sep. 26, 2000

[54] BALLOON CATHETER

[75] Inventors: Lily Chen Tu; Hosheng Tu, both of Tustin, Calif.

[73] Assignee: Polymerex Medical Corp., San Diego, Calif.

[21] Appl. No.: 09/184,558

[22] Filed: Nov. 2, 1998

[51] Int. Cl.[7] .............................. A61F 7/12; A61B 18/18
[52] U.S. Cl. ........................... 607/113; 606/41; 607/101; 607/102
[58] Field of Search ....................... 607/113, 96, 98–102; 600/585; 606/41, 49, 50, 108, 28, 39; 604/96, 97

[56] References Cited

U.S. PATENT DOCUMENTS

| | | | |
|---|---|---|---|
| 5,114,423 | 5/1992 | Kasprzyk et al. | 606/27 |
| 5,190,540 | 3/1993 | Lee | 606/28 |
| 5,383,853 | 1/1995 | Jung et al. | 604/96 |
| 5,456,662 | 10/1995 | Edwards et al. | 604/22 |
| 5,470,313 | 11/1995 | Crocker et al. | 604/96 |
| 5,752,932 | 5/1998 | Ellis et al. | 604/96 |
| 5,799,661 | 7/1998 | Clayman et al. | 606/39 |
| 5,814,061 | 9/1998 | Osborne et al. | 606/194 |
| 5,860,974 | 1/1999 | Abele | 606/41 |
| 6,004,269 | 12/1999 | Crowley et al. | 600/439 |

OTHER PUBLICATIONS

J. Cheung et al., "Molecular Organization and Electrical Properties of Mixed Langmuir–Blodgett Multilayer Thin Films of Polypyrrole", J.L. Bredas (ed.) Conjugated Polymer Materials, 91–99, Published by Kluwer Academic Publishers (1990).

E.W. Meijer et al., "Poly–1,2–Azepines by the Photopolymerization of Phenyl Azides" J.L. Bredas (ed.) Conjugated Polymer Materials, 115–131, Published by Kluwer Academic Publishers (1990).

J.H. Burroughes et al., "Semiconductor Device Physics in Conjugated Polymers" J.L. Bredas (ed.) Conjugated Polymer Materials, 221–245, Published by Kluwer Academic Publishers (1990).

H. Eckhardt et al., "Vinylene–Linked Low–Band–Gap Conducting Polymers" J.L. Bredas (ed.) Conjugated Polymer Materials, 305–320, Published by Kluwer Academic Publishers (1990).

R.H. Baughman et al., "Conducting Polymer Electromechanical Actuators" J.L. Bredas (ed.) Conjugated Polymer Materials, 559–582, Published by Kluwer Academic Publishers (1990).

Anna Berlin, "Heterocycle—Based Electroconductive Polymers", D.L. Wise (ed.) Electrical and Optical Polymer Systems, 47–49, Published by Marcel Dekker, Inc. (1998).

G. Sepra, "The Next Wave in Minimally Invasive Surgery" pp. 36–44, MD & DI Aug. 1998.

*Primary Examiner*—Michael Peffley
*Assistant Examiner*—Roy Gibson

[57] ABSTRACT

An ablation balloon catheter for treating tissues or atherosclerosis on a patient having a prior angioplasty procedure, the balloon catheter comprising a conductive elastomer electrode means which is coated onto a balloon surface and is connected to a radiofrequency current source to supply radiofrequency thermal therapy to the tissue for therapeutic ablation purposes.

16 Claims, 8 Drawing Sheets

BALLOON CATHETER

CROSS-REFERENCE TO RELATED APPLICATIONS

This application is a co-pending application of U.S. application Ser. No. 09/143,890, entitled "Ablation Apparatus and Methods for Treating Atherosclerosis" filed Aug. 31, 1998; Ser. No. 09/150,182, entitled "Rapid Exchange Stented Balloon Catheter Having Ablation Capabilities" filed Sep. 10, 1998; Ser. No. 09/157,360, entitled "Ablation Catheter and Methods for Treating Tissues" filed Sep. 19, 1998; Ser. No. 09/159,697, entitled "Ablation Device for Treating Atherosclerotic Tissues" filed Sep. 24, 1998; and Ser. No. 09/175,714 entitled" Dilatation Catheter Having a Bifurcated Balloon" filed Oct. 20, 1998 and are incorporated herein by reference.

TECHNICAL FIELD OF THE INVENTION

The present invention generally relates to improved medical apparatus and methods for treating vascular tissues, and more particularly, to a balloon catheter comprising conductive flexible electrodes on the balloon surface having RF ablation capabilities to treat tissues.

BACKGROUND OF THE INVENTION

An artery is one of the tube-shaped blood vessels that carries blood away from the heart to the body's tissues and organs. An artery is made up of an outer fibrous layer, a smooth muscle layer, a connecting tissue layer, and the inner lining cells. If arterial walls become hardened due to the accumulation of fatty substances, then blood flow can be diminished. Hardening of the arteries, or loss of vessel elasticity, is termed arteriosclerosis while fatty deposit build-up is termed atherosclerosis. Atherosclerosis and its complications are a major cause of death in the United States. Heart and brain diseases are often the direct result of this accumulation of fatty substances that impair the arteries' ability to nourish vital body organs.

The use of balloon catheters to treat stenosis or narrowing within various parts of the human body is well known. Balloon angioplasty is a nonsurgical method of clearing coronary and other arteries, blocked by atherosclerotic plaque, fibrous and fatty deposits on the walls of arteries. A catheter with a balloon-like tip is threaded up from the arm or groin through the artery until it reaches the blocked area. The balloon is then inflated, flattening the plaque and increasing the diameter of the blood vessel opening. The arterial passage is thus widened. As a result of enlarging the hardened plaque, cracks and lesions may unfortunately occur within the plaque to expose the underlying fresh tissue or denuded cells to the blood stream.

In one typical procedure, for example to dilate a stenotic region in a coronary artery, a relatively large guiding catheter is inserted into the patient's arterial system in the groin. The guiding catheter is then advanced through the arteries to a location near the patient's heart. A small wire guide is then inserted into the guiding catheter and advanced to the distal end of the guiding catheter, at which point it is steered to extend through the stenosis in the coronary arteries. A balloon catheter is then advanced over the wire guide until the deflated balloon lies across the stenosis. A working fluid is then pumped through the balloon catheter, thereby inflating the balloon and dilating the passage through the stenosis.

There are limitations, however, to this technique's application, depending on the extent of the disease, the blood flow through the artery, and the part of the anatomy and the particular vessels involved. Plaque build-up and/or severe re-stenosis recurs within 6 months is reportedly up to about 40 percent of those treated. Balloon angioplasty can only be characterized as a moderate-success procedure. Recently, a newer technique of inserting a metallic stenting element is used to permanently maintain the walls of the vessel treated at its extended opening state. Stents are tiny mesh tubes made of stainless steel or other metals and are used by heart surgeons to prop open the weak inner walls of diseased arteries. They are often used in conjunction with balloon angioplasty to prevent restenosis after the clogged arteries are treated. Stenting technique reduces the probability of restenosis; however, the success rate is still sub-optimal. The underlying fresh tissue or denuded cells still pose as a precursor for vessel spasms, reclosures or stenosis due to unknown reasons.

When a clogged artery is widened, the plaque is broken up and the underlying collagen or damaged endothelium is exposed to the blood flow. Collagen and/or damaged endothelium have a pro-thrombotic property that is part of body's healing processes. Unless the collagen or the damaged endothelium is passivated or modulated, the chance for blood vessel clotting as well as restenosis always exists. Moderate heat is known to tighten and shrink the collagen tissue as illustrated in U.S. Pat. No. 5,456,662 and U.S. Pat. No. 5,546,954. It is also clinically verified that thermal energy is capable of denaturing the tissue and modulating the collagenous molecules in such a way that treated tissue becomes more resilient ("The Next Wave in Minimally Invasive Surgery" MD&DI pp. 36–44, August 1998). Therefore, it becomes imperative to post-treat vessel walls after the walls are treated with angioplasty and/or stenting procedures.

One method of reducing the size of cellular tissues in situ has been used in the treatment of many diseases, or as an adjunct to surgical removal procedures. This method applies appropriate heat to the tissues, and causes them to shrink and tighten. It can be performed on a minimal invasive fashion, which is often less traumatic than surgical procedures and may be the only alternative method, wherein other procedures are unsafe or ineffective. Ablative treatment apparatus have an advantage because of the use of a therapeutic energy that is rapidly dissipated and reduced to a non-destructive level by conduction and convection, to other natural processes.

RF therapeutic protocol has been proven to be highly effective when used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after first locating the tissue sites for treatment. Radiofrequency energy, when coupled with a temperature control mechanism, can be supplied precisely to the electrode-to-tissue contact site to obtain the desired temperature for treating a tissue.

In the case of angioplasty alone, the enlarged blood vessel needs certain conductive tissue-contacting surface for delivering the RF thermal energy to the denuded collagen or damaged endothelium. A conductive elastomer electrode means can be coated or applied onto a rapid exchange balloon catheter or onto an over-the-wire balloon catheter, followed by connecting the conductive elastomer electrode means to a RF current source. It is useful in this case to shrink and tighten the target tissue through the conductive elastomer electrode means on the balloon surfaces by RF thermal therapy.

There is therefore a need in the prior art for a balloon catheter that may be used in association with a conductive elastomer electrode means on the balloon for angioplasty and tissue modulation purposes. The present invention is directed toward meeting this need for using the radiofrequency energy to treat a diseased artery or other tissues, such as esophagus, larynx, uterus, urethra and the like by a balloon means.

SUMMARY OF THE INVENTION

In general, it is an object of the present invention to provide a method and an improved medical ablation apparatus for generating heat, to treat the atherosclerosis, vascular vessels, or other tissues such as intestine, bile ducts, colon, ureter, uterine tubes, and the like. It is another object of this invention to provide a method and an apparatus for treating atherosclerosis, vascular walls, or tubular cellular tissues in a patient by a balloon catheter, whose surface is coated with an electrically conductive elastomer electrode means. It is a further object to apply RF current to the conductive elastomer electrode means on a balloon catheter and consequently to the underlying tissues. The conductive elastomer electrode means in this invention refers to an elastic polymer, which is electrically conductive and is suitable for use in RF ablation procedures. The surface-conductive balloon in this invention is generally referred to as a balloon that comprises a surface having conductive elastomer electrode means.

The conductive elastomer electrode means may include two general classes. The first class is a compounded elastomer, wherein the elastomer substrate contains homogeneously conductive fillers, such as silver-filled silicone, carbon-filled silicone, gold-filled silicone, carbon-filled polyurethane, conjugated silicone, and the like. The second class is a conducting polymer like polyacetylene or polypyrrole that shows an appreciable electrical conductivity after doping. A conductive elastomer electrode means is well known to one who is skilled in the art.

In one embodiment, it is an object of the present invention to relate a rapid exchange surface-conductive balloon catheter that allows exchange from a regular balloon angioplasty catheter to a surface-conductive balloon catheter without the need to replace the angioplasty catheter wire guide with an exchange-length wire guide before exchanging the catheters. It is another object of the present invention to provide a surface-conductive balloon as the dilatation balloon, in either an over-the-wire balloon type or a rapid-exchange balloon type balloon catheter.

A surface-conductive balloon catheter of the present invention is a catheter that comprises a conductive elastomer electrode means securely firmly attached, coated or coupled onto the balloon surface of said catheter. The conductive elastomer electrode means can be applied to the balloon surface to cover a portion or essentially the whole exterior surface of the balloon surface, or applied in a continuous manner on the balloon surface in a spiral pattern, a zigzag pattern, a mesh pattern, an axially straight pattern, a circumferentially straight pattern, other irregular pattern, and the like. Generally, the surface-conductive elastomer electrode means is terminated at a proximal point near the proximal end of a balloon, whereby the surface-conductive elastomer electrode means is coupled to an electrical conductor. Optionally, the electrical conductor is made of a conductive elastomer.

The thickness of the surface-conductive elastomer electrode means on the balloon surface is preferred to be a fraction of the balloon wall thickness. This is to provide a balloon catheter that is essentially "low-profile" when the balloon is deflated. In one optional embodiment, the surface-conductive elastomer electrode means is pre-stretched when attached or coupled to the balloon surface. In this manner, the conductive elastomer electrode means would exert certain retracting forces to the balloon when the balloon is deflated so as to keep the deflated balloon at its lowest profile. In another embodiment, the conductive elastomer substrate is mixed with the balloon raw material to make a balloon having electrical conductivity, adapted for RF applications.

In one embodiment, a rapid exchange surface-conductive balloon catheter comprises a catheter shaft defining an inflation lumen, the inflation lumen having a proximal end and a distal end. An inflatable balloon has a balloon surface, a balloon proximal end and a balloon distal end. A wire guide shaft defines a wire guide lumen, the wire guide shaft having proximal and distal ends, wherein the proximal end of the wire guide shaft is distal to the balloon distal end. A conductive elastomer electrode means is coated onto the balloon surface of said inflatable balloon. A catheter tip has a tip proximal end and a tip distal end, wherein the distal end of the inflation lumen opens into and is in communication with an interior of the inflatable balloon, the balloon distal end is sealed by the tip proximal end, and the wire guide shaft is coupled only to the catheter tip completely distally of the balloon distal end. In a further embodiment, the catheter system comprises a RF generator means and an electrical conductor, wherein the RF current is provided through the electrical conductor to the conductive elastomer electrode means. The surface-conductive balloon catheter includes a relatively short wire guide shaft that is bonded to the catheter shaft only at a location distal to the inflation lumen.

After a dilatation procedure, a surface-conductive balloon catheter rapidly exchanges a standard dilatation balloon catheter, wherein the conductive elastomer electrode means on the surface-conductive balloon catheter is connected through an electrical conductor to an external RF generator. The conductive elastomer electrode means is securely, firmly coated, attached or coupled on and/or around the deflated balloon of the surface-conductive balloon catheter and the catheter is inserted into the patient's body to a location of the stenosis. When the balloon of the surface-conductive balloon catheter is inflated, the conductive elastomer electrode means is deformed to a deployed condition on the exterior surface of the inflated balloon to contact the inner wall of the vascular vessel. An external RF current generator is provided to supply RF current to the deployed conductive elastomer electrode means to effect the RF ablation. After completing ablation therapy, the balloon is deflated and the conductive elastomer electrode means is reversibly un-deployed. The conductive-surface balloon catheter is withdrawn from the body.

In another embodiment, the surface-conductive balloon is used to substitute a standard dilatation balloon catheter in the angioplasty procedures. Following a standard dilatation procedure, an external RF current generator is provided to supply RF current to the deployed conductive elastomer electrode means on the inflated balloon to effect the RF ablation. After completing the dilatation/ablation procedure, the balloon is deflated and the conductive elastomer electrode means is reversibly undeployed. The conductive-surface balloon catheter is withdrawn from the body.

For illustration purposes of a rapid exchange balloon catheter procedure, in a typical balloon angioplasty procedure, after the stenosis has been dilated, the balloon angioplasty catheter and wire guide are removed from the guiding catheter and a second wire guide, or exchange wire guide, is inserted through the guiding catheter and steered to the stenosis location. The exchange wire guide is more than twice as long as the surface-conductive balloon catheter because it is necessary that the wire guide protrudes from the patient's body by a length greater than the length of the surface-conductive balloon catheter. This allows the exchange wire guide to be held steady with the physician's hand while the surface-conductive balloon catheter is advanced over the exchange guide wire. Once the distal end of the surface-conductive balloon catheter has been placed within the area of the dilated stenosis; the balloon of the surface-conductive balloon catheter may be inflated, thereby temporarily deploying the conductive elastomer electrode means in the region of the dilated stenosis. RF current is then provided to the conductive elastomer electrode means for therapeutic purposes. The balloon of the balloon catheter is deflated, allowing the balloon catheter along with the collapsed conductive elastomer electrode means to be withdrawn. The exchange wire guide and the guiding catheter are then withdrawn, thereby completing the operation.

It is another object of the present invention to provide a surface-conductive balloon over a wire means, wherein the wire means has a proximal end and a distal section with a distal end. In one embodiment, the surface-conductive over-the-wire balloon catheter is inserted into a body lumen through a guide wire, wherein the guidewire is steerable so that the distal end is deflected to the stenotic region. It is still another object of this invention to provide a method and a surface-conductive balloon catheter for treating atherosclerotic tissues at a vascular vessel by deploying the surface-conductive balloon in place, followed by RF ablation therapy.

The surface-conductive balloon generally includes two broad classes. One class is considered noncompliant balloon, formed from a generally nondistensible material such as polyethylene, polyethylene terephthalate, polypropylene, cross-linked polyethylene, polyimide, and the like. The other class is considered compliant balloon, formed from a generally complaint material such as nylon, silicon, latex, polyurethane, and the like.

In a further embodiment, it is another object of the present invention to provide a surface-conductive bifurcated balloon over a wire means, wherein the wire means has a proximal end and a two-head distal section with two distal ends. In an alternate embodiment for a surface-conductive bifurcated balloon, the wire means comprises two wires, each wire having its own distal end, and its own proximal end, wherein each wire is independently controlled. In one embodiment, the surface-conductive bifurcated balloon catheter is inserted into a body lumen through a pair of guidewires, wherein each guidewire is steerable so that both distal ends are either deflected in the same direction or in two separate directions at the bifurcation region. It is still another object of this invention to provide a method and a surface-conductive bifurcated balloon catheter for treating atherosclerotic tissues at the bifurcated region of vascular vessels by deploying the conductive elastomer electrode means in place, followed by RF ablation therapy. The "bifurcated balloon" in this invention is referred to as a balloon having a proximal end and a two-head distal section with two distal ends. In an alternate embodiment, the "bifurcated balloon" in this invention is also referred to as a balloon having two axially oriented compartments, each compartment has a proximal end and a distal end, wherein a portion of the two compartments near their distal ends is separated and a portion of the two compartments near their proximal ends is joined and stuck together. The joining of the two compartments can be achieved by use of glues, epoxy, adhesives, or thermal fusion. The two compartments are optionally not communicable.

In principles, heat is generated by supplying a suitable energy source to a surface-conductive balloon catheter, which is comprised of at least one surface-conductive balloon, in contact with the body tissues through the conductive elastomer electrode means of a surface-conductive balloon catheter. A suitable energy source may consist of radiofrequency energy, microwave energy, ultrasonic energy, alternating current energy, or laser energy. The energy can be applied to the conductive elastomer electrode means and consequently to the atherosclerosis, vascular walls, or cellular tissues. A DIP (dispersive indifferent pad) type pad or electrode, that contacts the patient, is connected to the Indifferent Electrode Connector on a RF generator. Therefore, the RF energy delivery becomes effective when a close circuit from a RF generator through a patient and returning to the RF generator is formed. When using an alternating current outlet, the generator should be grounded to avoid electrical interference. Heat is controlled by the power of the RF current delivered and by the delivery duration. The standard RF current generator means and its applications through a conductive electrode means, to a patient are well known for those who are skilled in the art.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 6, what is shown is an embodiment of a surface-conductive balloon catheter system, comprising applying radiofrequency energy therapy to treat the atherosclerosis, vascular vessels, or other tubular cellular tissues of a patient through a deployed conductive elastomer electrode means securely coupled onto the balloon of a surface-conductive balloon catheter.

Figure 1:
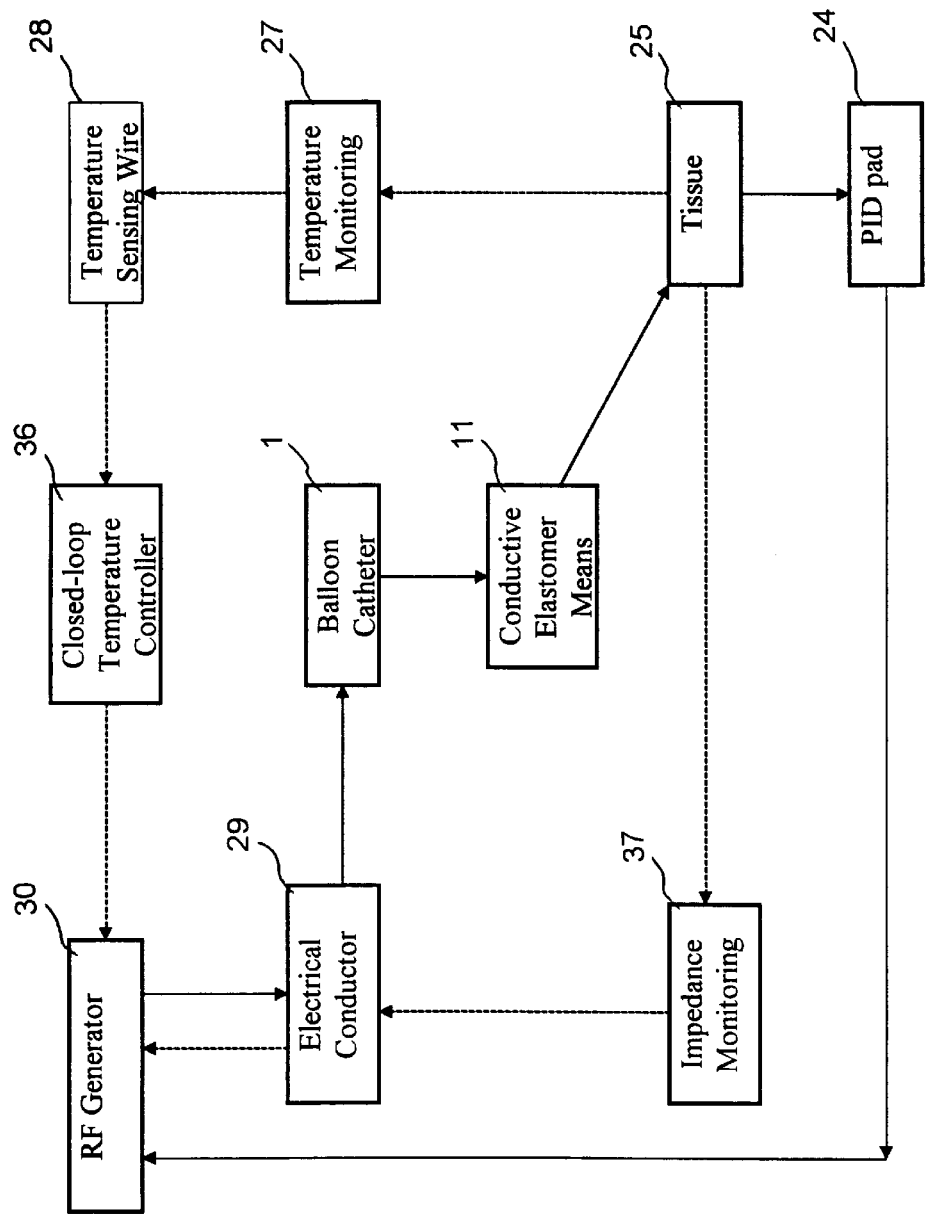
FIG. 1 is a schematic diagram of a RF treatment method in relation to a tissue or an atherosclerotic tissue through a conductive elastomer electrode means of a surface-conductive balloon catheter.

FIG. 1 shows a schematic diagram of a RF treatment method in relation to a tissue or an atherosclerotic tissue through a deployed surface-conductive balloon in a patient. A RF generator 30 is connected to a catheter 1 through an electrical conductor 29. A deployed balloon of the catheter 1 is to expand an electrically conductive elastomer electrode means 11 when the catheter is in a deployed state. The conductive elastomer electrode means 11 in different patterns on the balloon surface is in close contact with the underlying tissue 25. A DIP (dispersive indifferent pad) type pad 24 that contacts a patient is connected to the Indifferent Electrode Connector on the RF current generator 30. Therefore, the RF current delivery becomes effective when a close circuit from a RF generator through a patient and returning to the RF generator is established. Impedance 37 measured from the tissue contact is to ensure good tissue contact for ablation, otherwise the RF power is cut-off when the impedance exceeds a pre-determined value. A temperature sensor 27 is optionally used to measure the tissue temperature and is relayed through a temperature sensing wire 28 to a closed-loop temperature controller 36 for controlling the ablative current delivered. Heat is controlled by the power of the RF energy delivered and by the delivery duration. The temperature for tissue modulation is generally in the range of 60–80° C.

Figure 2:
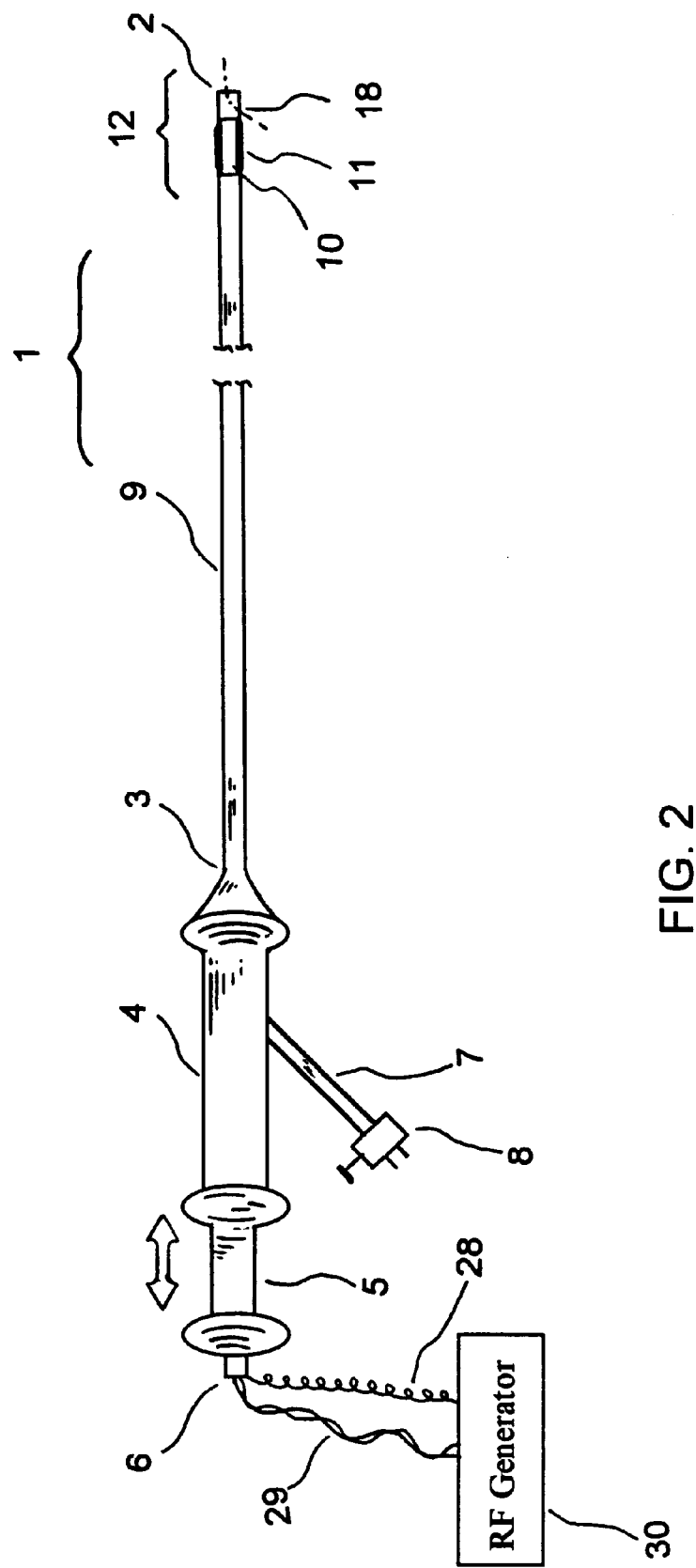
FIG. 2 is an overall view of a surface-conductive balloon catheter having a deployable balloon, a conductive elastomer electrode means, and a RF generator, constructed in accordance to the principles of the present invention.

FIG. 2 shows an overall view of a surface-conductive balloon catheter having a deployable balloon 10, a conductive elastomer electrode means 11, and a RF generator 30, constructed in accordance to the principles of the present invention. The surface-conductive balloon catheter system in the form of an elongate tubular assembly comprises a catheter shaft 9 having a distal section 12, a shaft distal end 2, a shaft proximal end 3, and at least one lumen 13 extending therebetween, wherein the at least one lumen has at least one opening at the distal section 12 of the catheter shaft 9. A handle or connector electrode means 4 is attached to the shaft proximal end 3 of the catheter shaft 9, wherein the handle 4 has a cavity. A hollow tubing 7 having a proximal end, a distal end, a passageway and a locking valve 8 is attached to the handle 4, wherein the passageway is connected to the at least one lumen 13 of the catheter shaft 9. In an alternate embodiment, the proximal end of the hollow tubing 7 preferably terminates with a standard female lure type fitting for attachment to a syringe for inflation and deflation of the inflatable balloon 10 by a working fluid.

Figure 3:
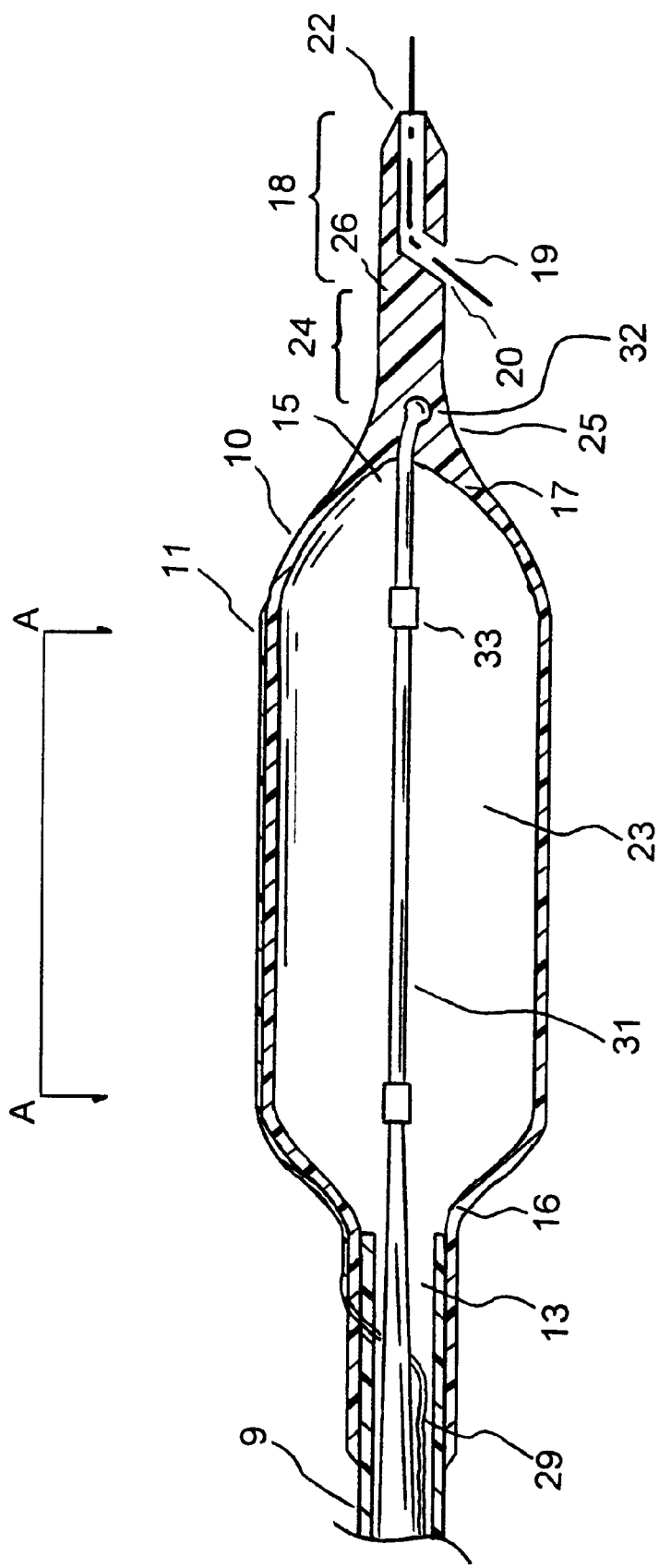
FIG. 3 is a cross-sectional view of the distal end portion of the surface-conductive balloon catheter, having a rapid exchange mechanism, a conductive elastomer electrode means on the inflated balloon, at a deployed state.
Figure 4A:
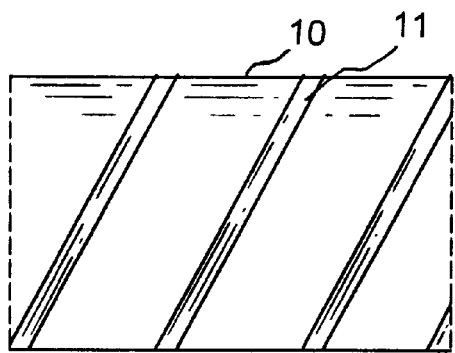
FIG. 4A is top-view of the balloon surface, showing a spiral pattern of the conductive elastomer electrode means of section A—A of FIG. 3.
Figure 4B:
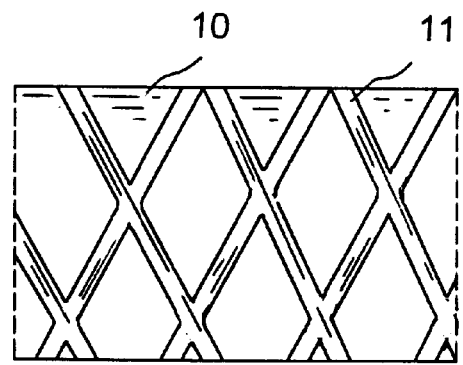
FIG. 4B is top-view of the balloon surface, showing a mesh pattern of the conductive elastomer electrode means of section A—A of FIG. 3.
Figure 4C:
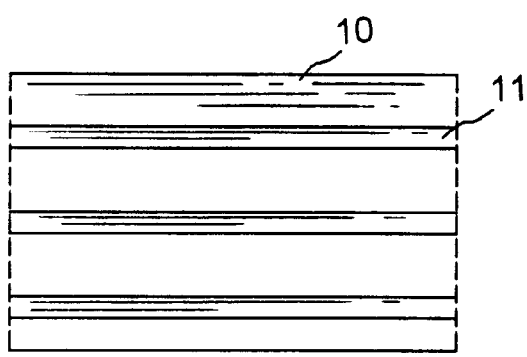
FIG. 4C is top-view of the balloon surface, showing an axially straight pattern of the conductive elastomer electrode means of section A—A of FIG. 3.
Figure 4D:
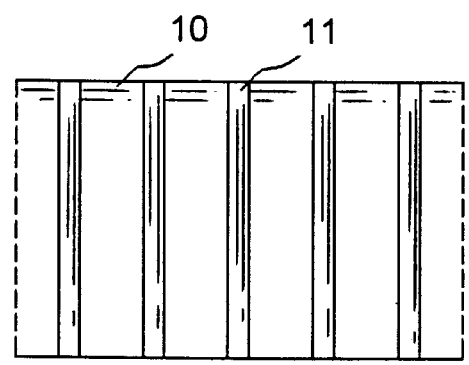
FIG. 4D is top-view of the balloon surface, showing a circumferentially straight pattern of the conductive elastomer electrode means of section A—A of FIG. 3.
Figure 4E:
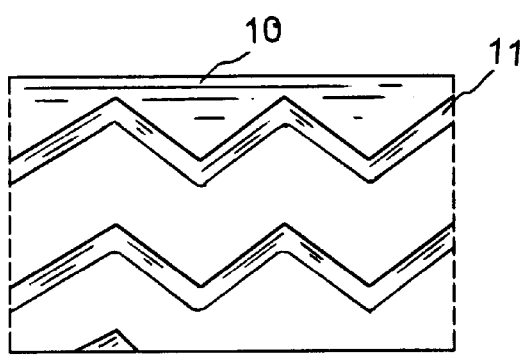
FIG. 4E is top-view of the balloon surface, showing a zigzag pattern of the conductive elastomer electrode means of section A—A of FIG. 3.
Figure 4F:
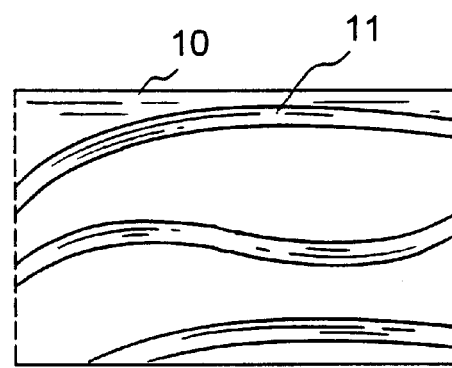
FIG. 4F is top-view of the balloon surface, showing a random pattern of the conductive elastomer electrode means of section A—A of FIG. 3.

As shown in FIG. 3, a rapid exchange type surface-conductive balloon catheter system comprises a catheter shaft 9 defining an inflation lumen 13, wherein the inflation lumen has a proximal end and a distal end 15. The inflation lumen 13 extends far enough in the proximal direction (not shown) in order to allow the proximal end of the catheter shaft 9 to be outside of the patient's body when the inflatable balloon 10 is placed across the stenosis. An inflatable balloon 10 has a proximal end 16 and a distal end 17.

A wire guide shaft 18 defines a wire guide lumen 19, the wire guide shaft having an open proximal end 20 and an open distal end 22 in order to allow a wire guide to pass therethrough, wherein the proximal end of the wire guide shaft is distal to the distal end 17 of the inflatable balloon 10. The proximal end 20 of the wire guide shaft 18 is formed at an angle to a transverse axis of the wire guide shaft 18. This reduces the chance of damage to the vessel wall as the catheter 1 is withdrawn.

A conductive elastomer electrode means 11 is securely and firmly coupled around said inflatable balloon 10, wherein an electrical conductor 29 is connected to said conductive elastomer electrode means 11. A catheter tip 24 has proximal end 25 and distal end 26, wherein the distal end 15 of the inflation lumen 13 opens into and is in communication with an interior 23 of the inflatable balloon 10, the distal end 17 of the inflatable balloon 10 is sealed by the proximal end 25 of the catheter tip 24, and the wire guide shaft 18 is coupled only to the catheter tip completely distally of the distal end 17 of the inflatable balloon 10. The distal end 17 of the inflatable balloon 10 is closed and merges into the catheter tip 24.

A stiffening wire 31 extends through the inflation lumen 13 and the interior 23 of the inflatable balloon 10 and terminates within the catheter tip 24. The stiffening wire 31 preferably includes a small ball or other enlargement 32 at its distal end in order to anchor the stiffening wire 31 within the catheter tip 24. The stiffening wire is preferably formed from stainless steel or Nitinol shape-memory superelastic material. At least one radiopaque marker band 33 is placed around the stiffening wire 31 near the proximal end 16 or the distal end 17 of the inflation balloon 10. The radiopaque marker band 33 may be made of any radiopaque material, such as gold, tungsten, silver or platinum. The location of the at least one radiopaque marker band 33 allows the position of the inflatable balloon 10 to be accurately determined by fluoroscopy in order to ensure proper positioning of the inflatable balloon prior to inflation.

The external RF generator 30 (shown in FIG. 2) is part of the balloon catheter system, wherein a RF current is provided at the connector 6 of the balloon catheter 1 through the electrical conductor 29 to the conductive elastomer electrode means 11. The RF current is preferably in the range of 50 kHz to 2,000 kHz.

The surface-conductive balloon 10 of the balloon catheter 1 is preferably formed from at least one of the following material: polyethylene, cross-linked polyethylene, polypropylene, polyimide, polyethylene terephthalate, and nylon. The conductive elastomer electrode means 11 of various patterns and materials become an integral part of the inflatable balloon 10.

The surface-conductive balloon catheter of the present invention can be used to deploy balloon-expanded conductive elastomer electrode means in several parts of the anatomy for further ablation therapy, and is not limited solely to the location of coronary arteries. For coronary arteries, the balloon diameter including its associated elastomer electrode means is generally in the range of 1.5 to 5 mm while the balloon length is generally 10 to 30 mm. The overall length of the catheter should be around 110 cm or longer and the stiffening wire should be approximately 0.010–0.015 inches in diameter. The distal end of the stiffening wire can be tapered in order to allow more flexibility at the distal end of the catheter shaft 9. The outside diameter of the catheter shaft 9 should be approximately 0.7 to 2.0 mm.

The surface-conductive balloon catheter is preferably formed by starting with a length of tubing, which is equal in cross-sectional dimensions to the desired dimensions of the catheter shaft 9. The distal end of this tubing is closed and a portion of the tubing is placed into a mold, which has the shape and dimensions of the desired size of the inflated balloon 10. The section of the tubing within the mold is then heated and the interior 23 of the tubing is pressurized such that the portion of the tubing within the mold expands to the interior dimensions of the mold. The tubing is then cooled such that the material within the mold retains the shape of the interior of the mold. The mold is then removed and the distal end of the tubing is cut distal to the distal end of the balloon at the desired distance. This will allow a portion of the distal end become the catheter tip 17. During molding, a stiffening wire 31, having at least one radiopaque marker band 33, can be inserted inside the lumen 13 all the way to the distal end 25 of the tubing so that the distal ball 32 is partially molded into the distal end of the catheter shaft 9. In one embodiment, the balloon has a variable diameter inflation profile. In another embodiment, the conductive elastomer substrate is mixed with the balloon raw material to make a balloon that is electrically conductive, adapted for RF applications.

A conductive elastomer in a solution form or melted form is coated and coupled onto the exterior surface of the balloon to form the conductive elastomer electrode means 11. FIG. 4A to FIG. 4F show top-views of the balloon surface 10 having a coated elastomer electrode means 11 with different preferred patterns: including a spiral pattern, a mesh pattern, an axially straight pattern, a circumferentially straight pattern, a zigzag pattern and a random pattern.

A second section of tubing having dimensions desired for the wire guide shaft 18 is then placed next to the catheter tip 24 such that the proximal end 20 of the wire guide shaft 18 is adjacent the distal end 26 of the catheter tip 24.

In one embodiment, at least one temperature sensing means 27 is disposed at close proximity of the deployed surface-conductive balloon 10. Insulated temperature sensor wire means 28 passes from the temperature sensing means 27, to an external temperature control mechanism 36 through an outlet connector 6. The RF current delivery is controlled by using the measured temperature from the temperature sensing means 27, through a closed-loop temperature control mechanism 36 and/or algorithm. When the measured temperature rises to a preset high-limit point, the temperature control mechanism sends out a signal to cut off the RF current supply. In a similar manner, when the measured temperature drops to a preset low-limit point, the temperature control mechanism sends out a signal to activate the RF current supply.

Figure 5:
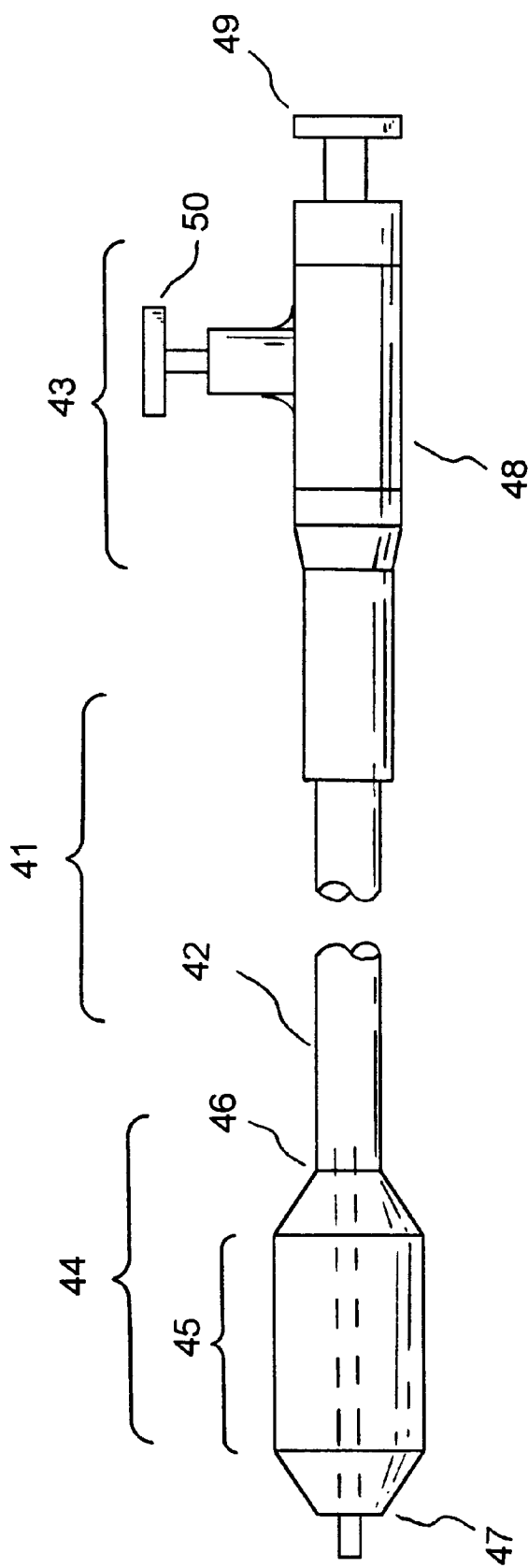
FIG. 5 is a schematic view of a preferred embodiment of a surface-conductive over-the-wire balloon catheter of one aspect of the present invention.

Alternatively, FIG. 5 shows a schematic view of a preferred embodiment of a surface-conductive over-the-wire balloon catheter 41 of one aspect of the present invention. A catheter comprising additional features known in the vascular dilatation art, such as implantable stents, drug delivery, perfusion and dilatation features, or any combination of these features, can be incorporated into the surface-conductive over-the-wire balloon of the present invention as will be readily apparent to one who is skilled in the art. A surface-conductive over-the-wire balloon catheter generally comprises an elongate flexible tubular body 42 extending between a proximal control end 43 and a distal functional end 44. The tubular body 42 may be produced in accordance with any known technique for manufacturing a balloon-tipped catheter body, such as by extrusion of a plastic material. In another embodiment, a portion or all of the length of tubular body 42 may comprise a spring coil, solid walled hypodermic needle tubing, braided reinforced wall tubing, or the like. The tubular body 42 is provided with a generally circular cross-sectional configuration having an external diameter in the range from about 0.06 cm to about 0.18 cm. The length is typically in the range of 100 cm to 150 cm. In another embodiment, generally triangular, oval or double-circular cross-sectional configurations can also be used, as well as other noncircular configurations depending upon the intended use.

Tubular body 42 must have sufficient structural integrity to permit the catheter to be advanced to distal arterial locations without buckling or undesirable bending of the tubular body. The tubular body may also need the ability to transmit torque and be flexible for passing through a bifurcated vascular vessel.

As illustrated in FIG. 5, the distal functional end 44 is provided with an inflatable surface-conductive over-the-wire balloon 45 having a proximal end 46 and a distal end 47. The proximal control end 43 of catheter 41 is provided with a manifold 48 having a plurality of access ports, as is known in the art. The manifold 48 is provided with a guidewire port 49 in an over the wire embodiment and a balloon inflation port 50. The surface-conductive over-the-wire balloon 45 can also be mounted on a rapid exchange type catheter, in which the proximal guidewire port 49 would be unnecessary as is understood in the art.

Figure 6:
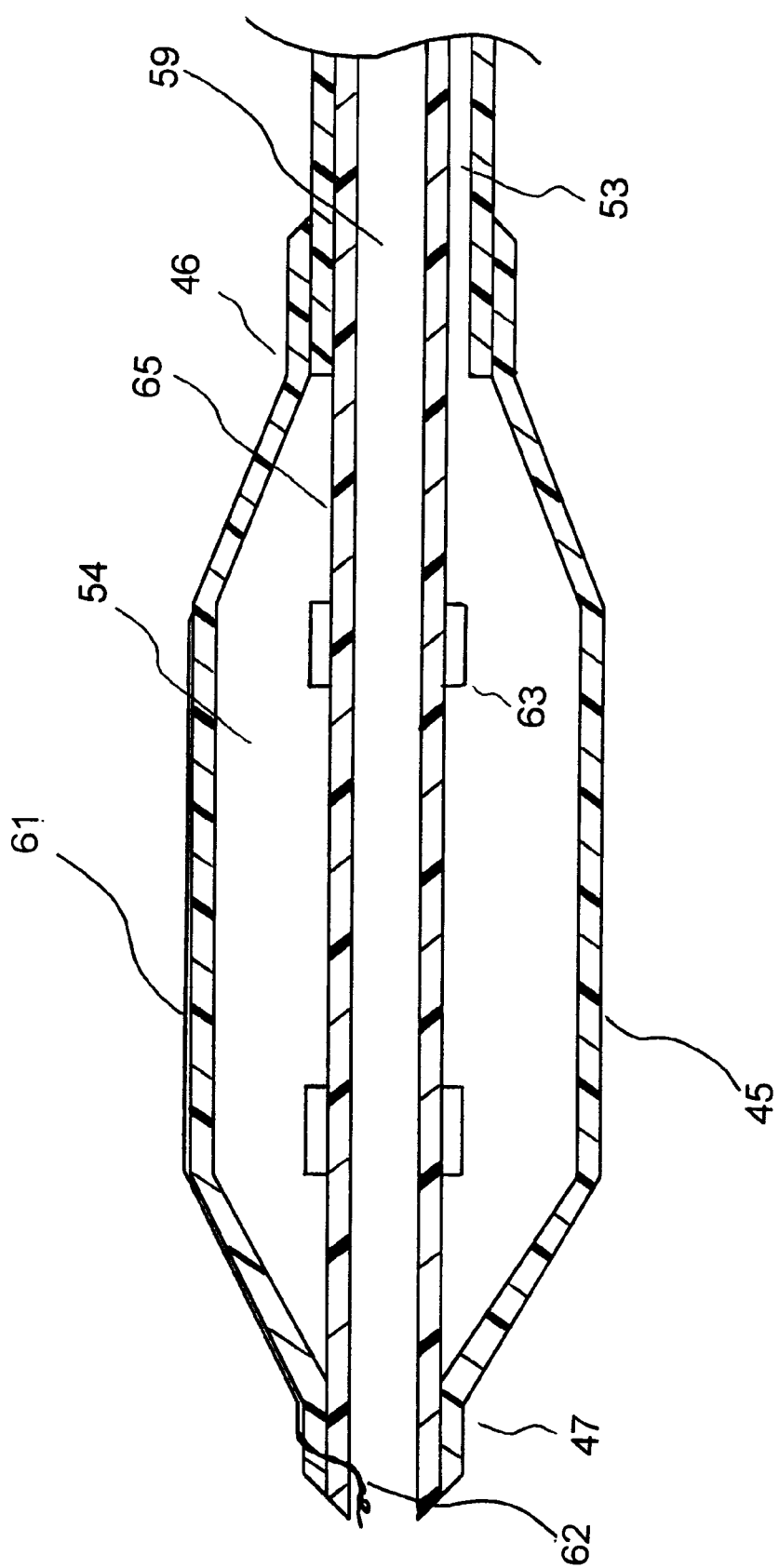
FIG. 6 is a partial cross-sectional view of a preferred embodiment of a surface-conductive over-the-wire balloon catheter of one aspect of the present invention.

Referring to FIG. 6, a partial cross-sectional view of a preferred embodiment of a surface-conductive over-the-wire balloon catheter 41 of the present invention is illustrated. Preferably, the tubular body 42 is provided with at least one guidewire lumen 59 extending all the way through the proximal end 46 of the balloon 45. The tubular body is also provided with an inflation lumen 53 extending into the proximal end 46 of the balloon 45, wherein the inflation lumen 53 is in communication with an interior 54 of the inflatable surface-conductive over-the-wire balloon 45, whereby the distal end 47 of the inflatable balloon 45 is sealed.

A conductive elastomer electrode means 61 is securely and firmly coupled around said inflatable surface-conductive over-the-wire balloon 45, wherein an electrical conductor 62 is connected to said conductive elastomer electrode means 61. At least one radiopaque marker band 63 is placed around the guidewire 65 near the proximal end 46 or the distal end 47 of the inflation balloon 45. The radiopaque marker band 63 may be made of any radiopaque material, such as gold, tungsten, silver or platinum. The location of the at least one radiopaque marker band 63 allows the position of the inflatable balloon 45 to be accurately determined by fluoroscopy in order to ensure proper positioning of the inflatable balloon prior to inflation.

For illustration purposes, a method of inserting a surface-conductive balloon catheter system into a patient's body for treating stenosis, the method comprising: inserting the surface-conductive balloon catheter at a non-deployed state into the patient's body to a location of stenosis; deploying the inflatable balloon; providing RF current to the conductive elastomer electrode means to treat the tissue; un-deploying the inflatable balloon; and withdrawing the surface-conductive balloon catheter from the patient's body.

The external RF current generator means has the capability to supply RF current by controlling the time, power, and temperature through an optionally separate closed-loop temperature control means. The patient is connected to the RF generator means through a DIP electrode to form a closed-loop circuit system. Therefore, RF current is applied and delivered to the targeted atherosclerosis region, through the deployed surface-conductive balloon of this invention. The radiofrequency energy current in this invention is preferably within the range of 50 to 2,000 kHz. By simultaneously applying RF energy to the deployed conductive elastomer electrode means and by applying the pressure against the underlying tissues by the deployed surface-conductive balloon, the tissues can be treated.

From the foregoing description, it should now be appreciated that an ablation catheter system for the atherosclerosis and the treatment of vascular tissues, comprising a suitable energy therapy and angioplasty has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A balloon catheter system, comprising:
   a catheter shaft defining an inflation lumen, the inflation lumen having a proximal end and a distal end;
   an inflatable balloon having a balloon surface, a balloon proximal end and a balloon distal end;
   a wire guide shaft defining a wire guide lumen, the wire guide shaft having proximal and distal ends, wherein the proximal end of the wire guide shaft is distal to the balloon distal end;
   a conductive elastomer electrode means coated onto the balloon surface of said inflatable balloon, wherein the conductive elastomer electrode means comprises an elastic polymer that is electrically conductive; and
   a catheter tip having tip proximal and tip distal ends, wherein the distal end of the inflation lumen opens into and is in communication with an interior of the inflatable balloon, the balloon distal end is sealed by the tip proximal end, and the wire guide shaft is coupled only to the catheter tip completely distally of the balloon distal end.

2. The balloon catheter system as in claim 1 further comprising a RF generator means and an electrical conductor, wherein RF current is provided through the electrical conductor to the conductive elastomer electrode means.

3. The balloon catheter system of claim 2, wherein the RF current is in the range of 50 kHz to 2,000 kHz.

4. The balloon catheter system of claim 1, wherein the conductive elastomer electrode means is made of material selected from the group of silver-filled silicone, carbon-filled silicone, gold-filled silicone, carbon-filled polyurethane, and conjugated silicone.

5. The balloon catheter system of claim 1, wherein the conductive elastomer electrode means on the balloon surface is made in one of the patterns of a spiral pattern, a zigzag pattern, a meshed pattern, an axially straight pattern, a circumferentially straight pattern, and an irregular pattern.

6. The balloon catheter system of claim 1, further comprising a stiffening wire having proximal and distal ends, wherein the stiffening wire extends through an interior of the inflatable balloon.

7. The balloon catheter system of claim 6, further comprising a spherical ball coupled to the distal end of the stiffening wire.

8. The balloon catheter system of claim 6, further comprising at least one radiopaque marker band coupled to the stiffening wire.

9. The balloon catheter system of claim 2, wherein the electrical conductor is a conductive elastomer.

10. The balloon catheter system of claim 1, wherein the balloon is made of material selected from the group consisting of polyethylene, cross-linked polyethylene, polyethylene terephthalate, polyimide, polypropylene, and nylon.

11. A balloon catheter system, comprising:
    a catheter shaft defining an inflation lumen, the inflation lumen having a proximal end and a distal end;
    an inflatable balloon having a balloon surface, a balloon proximal end and a balloon distal end, wherein the inflatable balloon is made by mixing a conductive elastomer substrate with a balloon raw material and by extruding the mixture to make the balloon that is electrically conductive, wherein said conductive elastomer substrate is selected from the group consisting of silver-filled silicone, carbon-filled silicone, gold-filled silicone, carbon-filled polyurethane, and conjugated silicone;
    a wire guide shaft defining a wire guide lumen, the wire guide shaft having proximal and distal ends, wherein the proximal end of the wire guide shaft is distal to the balloon distal end; and
    a catheter tip having tip proximal and tip distal ends, wherein the distal end of the inflation lumen opens into and is in communication with an interior of the inflatable balloon, the balloon distal end is sealed by the tip proximal end, and the wire guide shaft is coupled only to the catheter tip completely distally of the balloon distal end.

12. A balloon catheter comprising:
    an elongate, flexible, tubular body; and
    an inflatable balloon on the tubular body, wherein the balloon has a balloon surface, a proximal end and a distal end; and
    a conductive elastomer electrode means coated onto the balloon surface of said inflatable balloon, wherein the conductive elastomer electrode means comprises an elastic polymer that is electrically conductive.

13. The balloon catheter system as in claim 12 further comprising a RF generator means and an electrical conductor, wherein RF current is provided through the electrical conductor to the conductive elastomer electrode means.

14. The balloon catheter system of claim 12, wherein the conductive elastomer electrode means is made of material selected from the group of silver-filled silicone, carbon-filled silicone, gold-filled silicone, carbon-filled polyurethane, and conjugated silicone.

15. The balloon catheter system of claim 12, wherein the conductive elastomer electrode means on the balloon surface is made in one of the patterns of a spiral pattern, a zigzag pattern, a meshed pattern, an axially straight pattern, a circumferentially straight pattern, and an irregular pattern.

16. The balloon catheter system of claim 12, wherein the balloon is made of material selected from the group consisting of polyethylene, cross-linked polyethylene, polyethylene terephthalate, polyimide, polypropylene, and nylon.

* * * * *